United States Patent [19]

McBride

[11] Patent Number: 4,909,179

[45] Date of Patent: Mar. 20, 1990

[54] FLEXIBLE POROUS WEB HAVING A PERMANENT HUMIDITY SENSOR FOR INDICATING RELEASE OF MATERIAL THEREFROM

[75] Inventor: James F. McBride, Cleves, Ohio

[73] Assignee: The Stearns Technical Textiles Company, Cincinnati, Ohio

[21] Appl. No.: 185,416

[22] Filed: Apr. 25, 1988

[51] Int. Cl.$^4$ .............................................. G08B 5/00
[52] U.S. Cl. .................... 116/206; 116/200; 116/207
[58] Field of Search .............. 116/206, 200, 207; 428/913, 290, 305.5; 252/963, 8.8; 427/242; 73/73

[56] References Cited

U.S. PATENT DOCUMENTS

| | | | |
|---|---|---|---|
| 2,210,862 | 8/1940 | Tronstad | 34/95.1 |
| 3,121,615 | 2/1984 | Price | 422/56 |
| 3,173,880 | 3/1965 | Pappas | 436/40 |
| 3,499,316 | 3/1970 | Krause | 73/61.1 R |
| 3,533,277 | 10/1970 | Krause | 73/61.1 R |
| 3,607,782 | 9/1971 | Rosen | 436/40 |
| 3,676,199 | 7/1972 | Hewitt et al. | 428/213 |
| 3,770,362 | 11/1973 | Shaffer | 431/13 |
| 3,895,128 | 7/1975 | Gaiser | 428/43 |
| 3,952,746 | 4/1976 | Summers | 604/361 |
| 4,007,300 | 2/1977 | McQueary | 427/242 |
| 4,012,540 | 3/1977 | McQueary | 427/242 |
| 4,063,452 | 12/1977 | Bradshaw | 73/73 |
| 4,070,520 | 1/1978 | Volz et al. | 428/160 |
| 4,106,166 | 8/1978 | Henning | 28/103 |
| 4,150,570 | 4/1979 | Fuller | 73/335 |
| 4,389,448 | 6/1983 | Green | 428/195 |
| 4,460,644 | 7/1984 | Pavlich | 428/314.4 |

Primary Examiner—William A. Cuchlinski, Jr.
Assistant Examiner—W. Morris Worth
Attorney, Agent, or Firm—Wood, Herron & Evans

[57] ABSTRACT

A porous web having a permanent humidity detecting sensor is disclosed in which a metal salt is permanently bonded in the porous web matrix. The metal salt undergoes a color change from its hydrated to its dehydrated state to detect a change in humidity of a surrounding environment. Nonwoven fibrous webs having a permanent humidity detecting sensor are especially adapted for containing materials such as fabric softeners that may be released upon the conditions of a conventional clothes dryer for treatment of the clothes and visual detection of the release of softener by color change of the humidity sensor.

10 Claims, 1 Drawing Sheet

FLEXIBLE POROUS WEB HAVING A PERMANENT HUMIDITY SENSOR FOR INDICATING RELEASE OF MATERIAL THEREFROM

BACKGROUND OF THE INVENTION

Humidity sensing devices have been proposed which use inorganic chemical salt compositions that change color in response to relative humidity. A number of patents have issued that disclose such devices as illustrated by U.S. Pat. Nos. 2,210,862; 3,121,615; 3,173,880; 3,499,316; 3,533,77; 3,607,782; 3,770,362; 3,952,746 and 4,150,570. A number of difficulties have been presented by prior art sensing devices including inadequate visual perception of color changes, uniformity of color indicator dispersion and permanency of the humidity sensing capability. While a number of improvements have been achieved over the years in connection with such humidity sensing devices, further improvements are needed, especially as they may pertain to new fields of use where different problems confront the person of skill working in such fields.

SUMMARY OF THE INVENTION

This invention pertains to a new porous web having a permanent humidity sensor secured therein which is responsive to relative humidity changes. A metallic salt is permanently bonded in the porous web by means of a polymeric binder material whereby the metallic salt changes color when passing from a hydrated to a dehydrated state and such color change is reversible due to the permanency of the salt in the polymer matrix. The polymeric binder and metallic salt are selectively or uniformly dispersed throughout the porous web, thereby achieving a perceptive humidity change and yet the porous web has a high degree of permeability or porosity so that air flow is not substantially impeded therethrough. Such porosity permits other agents, such as fabric softeners, to be incorporated into the porous web for use in conventional laundry dryers.

A most preferred form of the invention is a flexible porous web for delivery of a fabric conditioning agent during a drying cycle where the humidity sensor color change indicates a satisfactory release of the fabric conditioner from the web. In this form, a nonwoven porous web of staple fibers is bonded principally at the intersections of said fibers with a polymeric binder system for a metal salt humidity sensor whereby the porosity of the web is substantially maintained. The web may also contain a fabric conditioning agent such as a fabric softener that has a softening point that closely matches the color change of the humidity sensor such that one may detect a release of fabric softener from the web by the color change. In this form of the invention, the fabric conditioner is bound in the matrix for release at the higher dryer temperatures yet below the deterioration point of the polymer matrix that binds the humidity detecting metal salt in the web. Thus, the clothes are not stained by the colored metal salt due to its permanency in the web and the user my determine when the fabric conditioner is properly dispensed in the drying cycle. The fabric softener melts for release from the web onto the clothes at about the color change of the salt. The substantial web porosity provides sufficient void volume on the order of about 40 to 90% to absorb materials such as fabric conditioners for release therefrom. In the case of a fabric softener-containing web, a void volume of at least about 75% is desirable so that there is no restriction of normal air flow volume through the dryer.

DETAILED DESCRIPTION OF THE INVENTION

The preferred porous webs of this invention are nonwoven webs of fibrous materials, although other web substrates such as spun bonded or paper substrates and woven fabrics or equivalent cellular or synthetic foam substrates may be employed to produce a permanent humidity sensor therein and still maintain a substantial porosity or void volume. Nonwoven webs are formed from organic textile fibers such as cotton, wool, wood, jute, viscous rayon, nylon, polyester, carbon, or other materials. Inorganic fibers can be used such as glass and metal. In the case of staple fibers, fiber length varies from about $\frac{1}{4}$ inch to about 2 or more inches. In the case of spun bonded webs, the fiber lengths are indefinite. Such staple fibers are processed through conventional textile machinery. For example, a carding machine may be used to form a continuous length of rather two-dimensional loosely associated fibers known as a carded web. These webs may be assembled to form a multiple layer or three-dimensional fibrous web of significant weight, e.g., from about several hundred grains to thousands of grains per yard. In continuous nonwoven fibrous webs, the textile fibers are arrayed at various angles to the lengthwise axis of the web. When a web is formed by the action of a carding machine, the fibers are usually predominantly oriented in the machine direction and, on the other hand, isotropic webs may be formed such as by air-laying. Carding or air-laying machines produce somewhat standardized fibrous web widths and, if necessary, such widths may be expanded. U.S. Pat. No. 4,106,166 is an example of a method and apparatus for expanding the width of preformed fibrous webs for use in making a permanent humidity sensor of this invention.

The nonwoven fibrous webs above described are impregnated with a polymeric binding agent and a metal salt humidity detecting compound. The polymeric binder permanently binds the metal salt to the web and yet permits metal salt to reversibly become hydrated/dehydrated so that the color change may be visually detected. The polymeric material is selected to trap the salt and regulate the rate of hydration/dehydration. Solvent soluble or reversible dyes and opacifiers may be added to the binder system to give a range of colors and shades. In a preferred form, the polymeric binders are applied as emulsions of acrylic, polyvinylacetate, or similar polymeric nature, and mixtures thereof. Preferably, these polymeric binders are self cross-linking such that the binder may be set upon drying or upon suitable pH control. A metallic salt such as cobaltous chloride which changes color when hydrated or dehydrated is included in the aqueous polymer emulsions. However, other metallic salts can be used depending upon the end application such as cobaltous chloride, cobaltous bromide, copper chloride, copper sulfate, nickel chloride, nickel ammonium chloride and nickel sulfate. The aqueous polymeric binder and metallic salt humidity detectors are suitably applied to the nonwoven fibrous web, most preferably during machine handling of the fibrous web at a saturation point in-line. Typically, upon running the web through a nip roll, the nip roll may be impregnated with the latex binder and metallic salt composition for saturation of the web. Upon microscopic examination of the web after latex bonding and subsequent drying or curing of the binder, the web is predominantly bonded at intersections of fibers by accumulation of binder throughout the porous matrix. The polymeric binder traps the metallic salt throughout its matrix principally at the fiber or filament intersections of a web in a permanent fashion. Thus, a metallic salt is capable of serving as a permanent humidity detector in the porous web.

The porous web has a high degree of void volume, for example, about 40 to about 90%, so that air volumes may pass therethrough very readily. This property of permeability also permits fabric conditioning agents or other materials to be deposited selectively or uniformly throughout the web for dispensing from the web. In a preferred form, fabric conditioning agents may be deposited in the web that melt or soften at dryer temperature cycles such that release of softening agent corresponds to the color change in the humidity detector. Typically, the softening agent will soften at dryer temperatures on the order of about 140° to 160° F. and this corresponds to the color change of a cobaltous chloride impregnated web. Wherefore, in a most preferred form, the invention offers a humidity detector operable in a conventional dryer cycle to detect dryness of the clothes and/or the release of fabric conditioning agents such as softeners to be deposited on the clothes. The user upon visually observing the color change will rest assured that the softening agent has been imparted to the dried clothes. The humidity detecting device of this invention can be employed for dispensing other materials in a similar fashion where the color change due to hydration/dehydration also reflects a property of the material being dispensed or treated by the web.

The choice of woven or nonwoven webs or cloths may vary as indicated above. The fibers of such webs may vary, but preferably are from regenerated cellulose, rayon, or other polyester, usually lubricated with standard textile lubricant. Preferably, the fibers are staple fibers as indicated above varying from about ¼ inch to about 2 inches in length and are from 1.5 to 5 denier. Preferably, the fibers are unwoven and substantially haphazardly oriented and adhesively bonded together with polymeric binder, for instance, especially a self cross-linking polymer system as indicated above. A nonwoven fabric having a weight on the order of about 10 to about 25 grams per square yard may be preferably employed containing about 25 to about 35% by weight of the polymer and metal salt solids. The air permeability of the porous web before and after impregnation is on the order of about 900 to 1100 cubic feet per minute. The web has a thickness on the order of about 5 to about 7 mils. The basis weight of the finished web containing the humidity sensor is from about 15 to about 25 grams per square yard. For a softener web, softener is contained to provide a total basis weight of about 30 to 60 grams/yd². A normal range of metal salt in the web is from about 0.01 to about 0.1 grams/yd², preferably about 0.05. The amount of metal salt sensor will depend upon the number of factors such as intensity of color, other opacifiers or ingredients present, and end use of the product.

The fabric softeners that may be employed in the fabric softening device of this invention can be selected from several classes of compounds: cationic quaternary ammonium salts including quaternary imidazolinium salts; nonionic compounds such as tertiary phosphine oxides, tertiary amine oxides and ethoxylated alcohols and alkylphenols; anionic soaps, sulfates and sulfonates, e.g., fatty acid soaps, ethoxylated alcohol sulfates and sodium alkyl sulfates, alkyl sulfonates, sodium alkylbenzene sulfonates and sodium or potassium alkylglycerylethersulfonates zwitterionic quaternary ammonium compounds; ampholytic tertiary ammonium compounds; and compatible mixtures of one or more compounds of these classes. Essential to the compositions of the fabric softeners is that they exhibit the softening point below the temperature of about 170° F., i.e., on the order of about 140° to about 160° F. such that they are preferentially operable in a clothes dryer. Because of their known softening efficacy, the most preferred cationic softening agents are dialkyldimethyl ammonium ethyl sulfate or chloride, where the alkyl contains from 12 to 20 carbon atoms and is derived from long chain fatty acids, especially from hydrogentted tallow. A number of such softeners are made available by Sherex Chemical Company under the trade names VARI-SOFT. For purposes of this invention, VARISOFT 136 (100%) which is a dihydrogenated tallow dimethyl ammonium methylsulfate may be employed. Hydrogenated tallow, i.e., $C_{14}$–$C_{18}$ fatty acids are employed as the long chain fatty acids along with methoxylated fatty acids of the same type. Other softeners are sold under the same trademark VARISOTT and are known to include methoxylated or propoxylated hydrogenated fatty acids. Methyl-1-alkyl amidoethyl-2-alyl imidazolinium methyl sulfate where the alkyl is $C_{17}$ saturated or unsaturated groups and the imidoethyl are $C_{18}$ saturated or unsaturated imido groups are employed. Reference is made to the book on "Household and Industrial Fabric Conditioners", edited by M.H. Gutcho, Noyes Data Corporation, Park Ridge, New Jersey (1980) in order to obtain other examples of suitable fabric conditioning agents and their methods of application to porous webs. U.S. Pat. Nos. 4,007,300 and 4,012,540 may be referred to, and are incorporated herein by reference, for other fabric conditioners.

BRIEF DRAWING DESCRIPTION

DETAILED OPERATING EXAMPLE

This invention was practiced by mixing the following ingredients in the order listed to form a uniform mixture having a pH on the order of about 7 and containing solids on the order of about 12.6 to about 13 percent for treatment of a porous web in accordance with the principles of this invention.

| INGREDIENTS | PARTS |
| --- | --- |
| Water | 2861.00 |
| Ammonium Chloride | 9.00 |
| Ammonium Hydroxide | 17.50 |
| SM-2162 | 1.00 |
| Triton X-100 | 2.50 |
| Sipex TDS | 2.00 |
| Leucophor AC | 0.75 |
| Rhoplex E-1402 | 495.00 |
| Suncryl RW-41 | 605.00 |
| Cymel Dispersion (9 parts Cymel 303 | 6.00 |

| INGREDIENTS | PARTS |
| --- | --- |
| and 1 part Triton X-100 premixed) | 5 |

As used in the above table, SM-2162 is a silicone release agent, Triton X-100 is a nonionic surfactant, Sipex TDS is also a surfactant, Leucophor AC is a brightener, Rhoplex E-1402 is an aqueous acrylic emulsion, Suncryl RW-41 is a polyvinyl acetate emulsion of the anionic self cross-linking copolymer type and Cymel Dispersion contains Cymel 303 which is hexamethoxymethylmelamine cross-linking agent. The ammonium chloride is a catalyst and the ammonium hydroxide was added for pH control at about 7. Cobaltous chloride was added in amount of about 1% by weight. This provides an optimum level in the preferred form of cobaltous chloride of about 0.04 to 0.05 grams per square yard of an 16–20 grams/yd$^2$ substrate.

Figure 1:
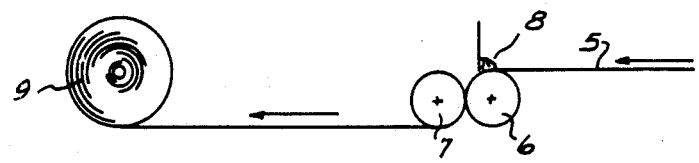
FIG. 1 is a diagrammatic view of an apparatus for impregnating a web with a permanent humidity sensor of this invention.
Figure 2:
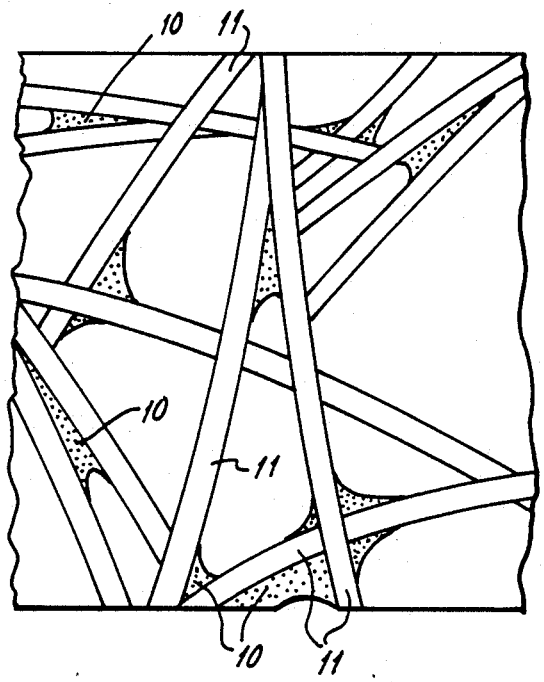
FIG. 2 is a magnified cross-sectional view of a finished web portion of FIG. 1 showing the permanently bound humidity sensor.

A nonwoven fibous web 5 of 100% rayon was then provided by a carding operation not shown in the drawing. This web 5 was comprised of lofty unbonded staple fibers having a weight of between about 11–14 grams/yd$^2$. Upon passing the web 5 on conventional equipment through nip rolls 6 and 7 on the order of about 300 feet per minute solids from the above solution on the order of about 28 to about 33% on the weight basis of the web were deposited uniformly by impregnating at 8 throughout the web. Upon drying or curing the web at a temperature of about 375° F., a nonwoven fibrous web having bonded cobaltous chloride uniformly throughout its matrix was provided on takeup roll 9. This web had a tensile of about 2500-3000 (dry MD) and about 400-600 (dry CD). The air permeability of the web was approximately 900-1100 CFM and it had a thickness of about 5 to about 7 mils. The void volume was about 85%. The air permeability of the web was substantially maintained by the void volume. FIG. 2 is a magnified view of about 500X of the finished web of FIG. 1 showing the binder and metal salt 10 substantially at the intersections of fibers 11. The web appeared white in color, yet upon being dryed, typically at temperatures on the order of about 140-170° F., the web color turned blue. Under these conditions, the cobaltous chloride change color when passing from the hydrated to the dehydrated state upon the application of heated dryer air. The polymeric material was employed to trap the salt and regulate the rate of hydration/dehydration. The hydration/dehydration of the metallic salt was reversible, therefore indicating the spent quality of the porous web. If desired, solvent soluble or dispersible dyes and opacifiers may be added to the impregnated web to give a range of colors and shades. Furthermore, the polymer solution containing the metallic salt humidity detector may be applied through saturation, glazing, foaming or printing onto the nonwoven fibrous web to obtain varying visibly detectable patterns on the web.

A fabric softener device may then be made employing the above web by applying a suitable fabric softener such as a disallow methyl ammonium chloride identified above (VARISOT 136). In a typical operation, the humidity detecting web may be immersed through a softener liquid in a pan. An aqueous alcohol softening formulation may be placed in the pan and kept in a melted condition by immersing the pan or container in a water bath heated to a temperature of about 150° F. As the fibrous web is passed through the softener liquid pan, suitable amounts of softener liquid are introduced into the web at a fabric softener impregnation weight of about 14 to 42 grams/yd$^2$. After passing through the pan and over rollers, the softener liquid, as impregnated into the fibrous web will rapidly cool down and harden upon evaporation of the water. Typically, isopropanol or suitable alcohol is also present in water in order to aid in the evaporation. The softener treated web had about 14–42 grams of fabric softener per square yard. Upon use of the fabric softened substrate in a laundry dryer at a normal temperature of 170° F., the fabric softener melted substantially at the color change in the web from white to blue. Accordingly, this example demonstrates the utility of the porous web of this invention in dispensing material or agents from the porous web that have been deposited therein at approximately the color change attributable to the humidity detector impregnated in the web.

In view of the above detailed description and the operating examples, variations will become apparent to the person of ordinary skill in this art in order to practice the invention and such variations are within the scope of this invention.

What is claimed is:

1. A porous web having a permanent humidity detecting sensor comprising
   a porous web having a substantially porous matrix and having bonded therein a metallic salt that undergoes a color change from its hydrated to its dehydrated state, said metallic salt bonded in said matrix with a polymeric binder that permanently bonds the salt in said matrix and allows the salt to undergo a visible color change upon a change in humidity of the environment to which it is exposed, said porous matrix containing an agent for release from the matrix, said release detected by a visual observation of said color change.

2. The device of claim 1 wherein said web is a nonwoven fibrous substrate formed from staple fibers wherein said polymeric binder binds said metallic salt and the fibers in the interstices of the porous matrix to substantially maintain the web porosity.

3. The device of claim 2 wherein said polymeric binder and metal salt are derived from an aqueous mixture of a polymeric emulsion containing the metallic salt.

4. The device of claim 3 wherein said polymeric emulsion is selected from the group consisting of acrylic and polyvinyl acetate emulsions, and mixtures thereof, and said metal salt is a soluble salt of cobalt.

5. The device of claim 4 wherein the cobalt salt is cobaltous chloride.

6. The device of claim 1 wherein said porous matrix has a void volume of about 40 to about 90%.

7. The device of claim 1 wherein said agent is a solid fabric softener that is released by melting at the drying temperatures of a conventional dryer.

8. The device of claim 7 wherein said fabric softener is uniformly contained in said matrix.

9. A porous web having a permanent humidity detecting sensor comprising
   a nonwoven porous web of staple fibers having a substantially porous matrix and having bonded therein a metallic salt that undergoes a color change from its hydrated to its dehydrated state, said porous matrix having a void volume of about 40 to about 90%, said metallic salt bonded in said matrix with a polymeric binder that permanently bonds the fibers and the salt in said matrix and allows the salt to undergo a visible color change upon a change in humidity of the environment to which it is exposed, said porous matrix containing an agent for release from the matrix, said release detected by a visual observation of said color change, said polymeric binder and metal salt are derived from an aqueous mixture of a polymeric emulsion containing the metallic salt.

10. The device of claim 9 wherein said agent is a solid fabric softener that is released by melting at the drying temperatures of a conventional dryer.

* * * * *